United States Patent [19]

Reinhardt et al.

[11] Patent Number: 6,100,405
[45] Date of Patent: Aug. 8, 2000

[54] BENZOTHIAZOLE-CONTAINING TWO-PHOTON CHROMOPHORES EXHIBITING STRONG FREQUENCY UPCONVERSION

[75] Inventors: Bruce A. Reinhardt, deceased, late of Tipp City; by Erin D. Reinhardt, administrator; by Jason A. Reinhardt, administrator, both of New Carlisle; Ramamurthi Kannan, Cincinnati, all of Ohio

[73] Assignee: The United States of America as represented by the Secretary of the Air Force, Washington, D.C.

[21] Appl. No.: 09/333,304

[22] Filed: Jun. 15, 1999

Related U.S. Application Data

[60] Provisional application No. 60/127,602, Mar. 16, 1999.

[51] Int. Cl.⁷ .................................................. C07D 277/66
[52] U.S. Cl. ......................... 548/160; 548/152; 548/224
[58] Field of Search .................................... 548/160, 152, 548/224

[56] References Cited

U.S. PATENT DOCUMENTS

| | | |
|---|---|---|
| 5,770,737 | 6/1998 | Reinhardt et al. . |
| 5,859,251 | 1/1999 | Reinhardt et al. . |

FOREIGN PATENT DOCUMENTS

| | | | |
|---|---|---|---|
| 04298596 | 10/1992 | Japan | ...................................... 548/101 |

OTHER PUBLICATIONS

B.A. Reinhardt, L.L. Brott, S.J. Clarson, A.G. Dillard, J.C. Bhatt, R. Kannan, L. Yuan, G.S. He and P.N. Prasad, Highly Active Two–Photon Dyes: Design, Synthesis, and Characterization toward Application, Chem. Mater. 1998, 10, 1863–1874, published Jul. 1, 1998.

*Primary Examiner*—Robert Gerstl
*Attorney, Agent, or Firm*—Charles E. Bricker; Thomas L. Kundert

[57] ABSTRACT

There are provided asymmetrical two-photon chromophores of the formula:

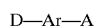

wherein Ar is selected from the group consisting of

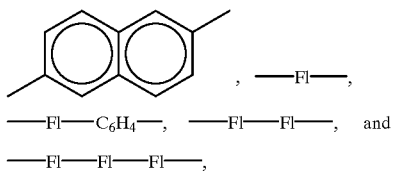

wherein Fl is a fluorene group of the formula:

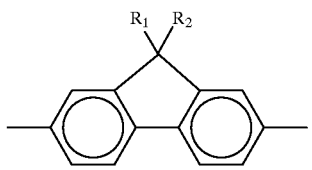

wherein $R_1$ and $R_2$ are alkyl groups having 2 to 20 carbon atoms, and wherein $R_1$ and $R_2$ are the same or different; wherein D is

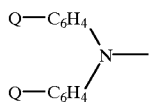

wherein Q is selected from the group consisting of —H, —OH and —O—$C_xH_{2x+1}$, wherein x has a value of 1 to 10; and wherein A is selected from the group consisting of

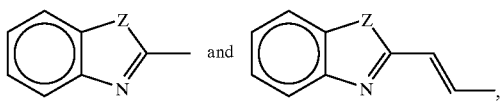

wherein Z is selected from the group consisting of —O— and —S—.

10 Claims, No Drawings

BENZOTHIAZOLE-CONTAINING TWO-PHOTON CHROMOPHORES EXHIBITING STRONG FREQUENCY UPCONVERSION

This application claims the benefit of U.S. Provisional application Ser. No. 60/127,602, filed Mar. 16, 1999.

RIGHTS OF THE GOVERNMENT

The invention described herein may be manufactured and used by or for the Government of the United States for all governmental purposes without the payment of any royalty.

BACKGROUND OF THE INVENTION

In ordinary fluorescence microscopy, defocused images outside the depth of focus are superimposed on an image formed on the focal plane. This globally lowers the contrast of microscopic image, which makes determination of fluorescence intensity difficult.

Confocal microscopy offers several advantages over conventional microscopy. The shallow depth of field, generally about 0.5 to 1.5 μm, of confocal microscopes allows information to be collected from a well defined optical section rather than from most of the specimen as in conventional light microscopy. Consequently, out-of-focus fluorescence is virtually eliminated, which results in an increase in contrast, clarity and detection.

In a point scanning confocal system, the microscope lens focus the laser light on one point in the specimen at a time, i.e., the focal point. The laser moves rapidly from point to point to produce a scanned image. Very little of the laser light falls on other points in the focal plane. Both fluorescent and reflected light from the sample pass back through the microscope. The microscope and the optics of the scanner compartment focus the fluorescent light emitted from the focal point to a secont point, called the confocal point. A pinhole aperature, located at the confocal point, allows light from the focal point to pass through to a detector. Light emitted from outside the focal point is rejected by the aperature. Accordingly, only the image near the focal plane inside the sample is obtained as a microscopic image.

In two-photon absorption excitation type laser scanning fluorescence microscopy, a laser beam forms an optical spot having a high energy density and the optical spot three-dimensionally scans the inside of a sample in the same manner as in confocal laser scanning fluorescence microscopy. Because of the arrangement, fluorescence due to excitation based on two-photon absorption appears only from a point where the optical spot is located inside the sample but no fluorescence due to excitation based on two-photon absorption appears from other portions. Therefore, there appears no defocused image other than one on the focal plane, which improves the contrast of the microscopic image.

Two-photon excitation is made possible by the combination of (a) the very high, local, instantaneous intensity provided by the tight focusing available in a laser scanning microscope, wherein the laser can be focused to diffraction-limited waist of less than 1 micron in diameter, and (b) the temporal concentration of a pulsed laser. A high intensity, long wavelength, monochromatic light source which is focusable to the diffraction limit such as a colliding-pulse, mode-locked dye laser, produces a stream of pulses, with each pulse having a duration of about 100 femtoseconds ($100 \times 10^{-15}$ seconds) at a repetition rate of about 80 MHz. These subpicosecond pulses are supplied to the microscope, for example by way of a dichroic mirror, and are directed through the microscope optics to a specimen, or target material, located at the object plane of the microscope. Because of the high instantaneous power provided by the very short duration intense pulses focused to the diffraction limit, there is an appreciable probability that a fluorophore (a fluorescent dye), contained in the target material, and normally excitable by a single high energy photon having a short wavelength, typically ultraviolet, will absorb two long wavelength photons from the laser source simultaneously. This absorption combines the energy of the two photons in the fluorophore molecule, thereby raising the fluorophore to its excited state. When the fluorophore returns to its normal state, it emits light, and this light then passes back through the microscope optics to a suitable detector.

The probability of absorption of two long wavelength photons from the laser source simultaneously is dependent upon the two-photon cross-section of the dye molecule. In U.S. Pat. No. 5,770,737, one of us describes asymmetrical fluorene-containing two-photon chromophores of the formula:

wherein the Ar core is

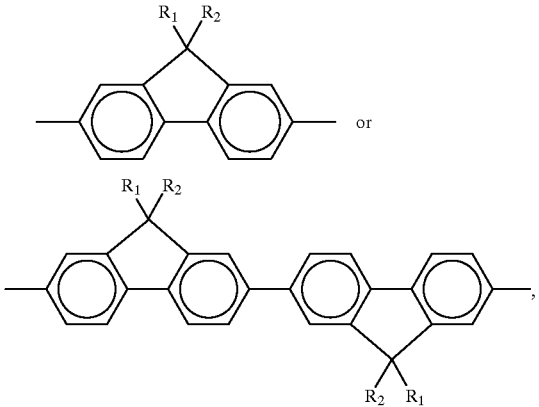

wherein $R_1$ and $R_2$ are alkyl groups having 8 to 12 carbon atoms, and wherein $R_1$ and $R_2$ are the same or different, wherein D is an electron donor moiety selected from the group consisting of

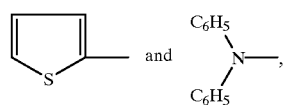

and wherein A is an electron acceptor moiety selected from the group consisting of

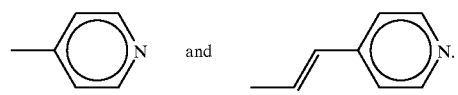

The most active dyes described in U.S. Pat. No. 5,770,737 incorporate an easily polarizable olefinic double bond in the backbone of the molecule. This olefinic bond, although it greatly increases the two-photon absorption (TPA) cross-section of chromophores, has limited thermal and photochemical stability, thus reducing the range of its utility. We have now discovered dyes with increased thermal and photochemical stability while maintaining the same level of two-photon activity.

Accordingly, it is an object of the present invention to provide new chromophores having large two-photon cross-sections and increased thermal and photochemical stability.

Other objects and advantages of the present invention will be apparent to those skilled in the art.

SUMMARY OF THE INVENTION

In accordance with the present invention there are provided asymmetrical two-photon chromophores of the formula:

D—Ar—A wherein Ar is selected from the group consisting of

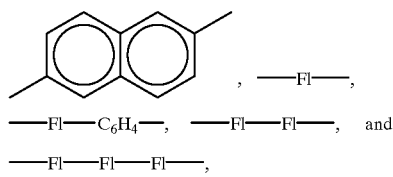

wherein Fl is a fluorene group of the formula:

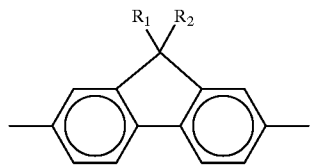

wherein $R_1$ and $R_2$ are alkyl groups having 2 to 20 carbon atoms, and wherein $R_1$ and $R_2$ are the same or different; wherein D is

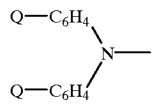

wherein Q is selected from the group consisting of —H, —OH and —O—$C_xH_{2x+1}$, wherein x has a value of 1 to 10; and wherein A is selected from the group consisting of

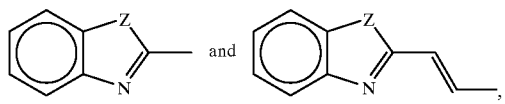

wherein Z is selected from the group consisting of —O— and —S—.

The following examples illustrate the invention:

EXAMPLE I

N-Phenyl-6-bromo-2-naphthylamine

Xylene was distilled from a mixture of 6-bromo-2-naphthol (16.4 g., 0.0735 mol.), aniline (25 ml, 0.274 mol.), xylene (25 ml), and p-toluene sulfonic acid monohydrate (2.7 g., 0.014 mol.) until the reaction temperature reached 190° C. The mixture was held at this temperature for 5 hours, and then cooled to 85° C. Sodium acetate (3.7 g.) and ethanol (100 ml) were added and the mixture was heated to reflux. The solution was cooled to 5° C. and the resulting slurry was filtered. The solids were washed with cold ethanol (50 ml). The air-dried solids (19.5 g.) were reslurried in hot water (150 ml) and filtered to give a gray solid, 19.3 g, 88% yield, m.p. 126.2–128.3° C. Two successive recrystalizations from heptane-ethyl acetate (19:1) gave a sample for analysis, m.p. 131–133° C. Mass Spec: m/z 297, 299 ($M^+$). Analysis: Calculated for $C_{16}H_{12}NBr$: C, 64.45; H, 4.06; N, 4.70, Br, 26.80. Found: C, 64.36; H, 4.02; N, 4.67; Br, 27.04.

EXAMPLE II

N,N-Diphenyl-6-bromo-2-naphthylamine

A mixture of N-phenyl-6-bromo-2-naphthylamine (29.8 g. 0.10 moles), iodobenzene (50 g. 0.245 mol.), potassium carbonate (60 g. 0.434 mol.), copper bronze (4.0 g. 0.063 g. atoms), 18-crown-6 (3.7 g. 0.014 mol.) and dichlorobenzene (100 ml) was kept under reflux for 3 hours under nitrogen, cooled and filtered. The residue remaining after concentration of the filtrate, was chromatographed over 600 g of silica gel. Elution with toluene-heptane (1:9), gave the product, 28.65 g., m.p. 135.8–137.4° C., in 77% yield. Mass Spec: m/z 373, 375 ($M^+$), 421 ($M^+$iodo). The product was contaminated with a small amount of the corresponding iodo compound. A sample recrystallized from heptane, m.p. 137.9–139.2° C. was analyzed. Analysis calculated for $C_{22}H_{16}NBr$: C, 70.59; H, 4.31; N, 4.09; Br, 21.35. Found: C, 69.23; H, 4.22; N, 3.61; Br, 20.56.

EXAMPLE III

N,N-Diphenyl-6-bromo-2-naphthaldehyde

To a mechanically stirred solution of N, N-Diphenyl-6-bromo-2-naphthylamine (18.7 g, 0.05 mol.), THF (150 ml), n-butyl lithium (1.6 M in hexanes, 38 ml, 60.8 mmol, 1.22 eq.) was added at −45° C. and the resulting thick creamy slurry was stirred for 30 minutes at this temperature. A solution of DMF (7 ml), in THF (30 ml.), was then added and the reaction temperature was maintained in the range −45 to −15° C. for a period of 2 hours. After allowing the reaction to come to room temperature, it was cooled to 5° C., treated with water (20 ml) and concentrated hydrochloric acid (5 ml). The yellow fluorescent solution was diluted with toluene (200 ml), the organic phase was washed with dilute bicarbonate solution, dried over magnesium sulfate and concentrated. The residual oil was chromatographed over 450 g. of silica gel. Elution with 1:1 toluene-heptane, followed by recrystallization from toluene-heptane gave the product 14.06 g, 87% yield, m.p. 108.2–109.9° C. I. R. KBr: 3061,1690,1621, and 1521 $cm^{-1}$. Mass Spec: m/z 323, ($M^+$). Analysis calculated for $C_{23}H_{17}NO$: C, 85.42; H, 5.30; N, 4.33. Found: C, 85.20; H, 5.12; N, 4.28.

EXAMPLE IV (6-(2-benzothiazol-2-ylvinyl)(2-naphthyl)) diphenylamine

A mixture of N,N-diphenyl-6-amino-2-naphthaldehyde (4.8 g, 0.015 mol.), 2-methyl benzothiazole (3.0 g, 0.020 mol.), powdered potassium hydroxide (18.0 g, 0.32 mol.) and DMSO (30 ml) was stirred at room temperature for 1 hour, poured into water, and the solids which separated were collected by filtration. These solids were purified by column chromatography on alumina using 1:3 toluene-heptane as the eluent, to give 3.6 g. of product (53% yield) m.p. 181.1–184.8° C. Recrystallization from 1:1 toluene-ethyl acetate raised the m. p. to 201.8–203.8° C. Mass Spec: m/z 454, (M+). Analysis calculated for $C_{31}H_{22}N_2S$: C, 81.92; H, 4.88; N, 6.16; S, 7.04. Found: C, 81.82; H, 4.93; N; 6.04, and S; 6.91.

EXAMPLE V (6-benzothiazol-2-yl(-naphthyl))diphenylamine

A mixture of N,N-diphenyl-6-amino-2-naphthaldehyde, (3.98 g., 0.0123 mol.), 2-aminothiophenol (1.5 ml, 0.014 mol.) and DMSO (20 ml) was heated to 180° C., held at this temperature for 45 minutes, and poured into water. The separated greenish solids were collected, air dried, transferred to a column of silica gel and eluted with 2:1 toluene-heptaneto get the product, 3.91 g. (74% yield), m.p. 186.1–187.3° C. Recrystallization from 1:1 toluene-heptane raised the m.p. to 188.1–189.5° C. Mass Spec: m/z 428 (M+). Analysis calculated for $C_{29}H_{20}N_2S$: C, 81.29; H, 4.70; N, 6.54; S, 7.47. Found: C, 81.04; H, 4.88; N, 6.62; S, 7.31.

EXAMPLE VI 9,9-Diethyl-2,7-dibromofluorene

To a mechanically stirred mixture of 2,7-dibromofluorene (66.5 g., 0.205 mol.), powdered potassium hydroxide (56.0 g., 1.0 mol.), potassium iodide (3.4 g.) and DMSO (150 ml), cooled to 10° C., ethyl bromide (40 ml, 58.4g. 0.536 mol.) was added dropwise over 45 minutes. The mixture turned from red to light purple. After allowing the temperature to warm to 20° C., the mixture was left overnight to stir and poured into water, 77.0 g.(98.7% yield), m.p. 144–153° C. The product was then recrystallized from hexane (550 ml) with charcoal treatment, and collected in two crops, m.p. 154–157° C. and 153–154° C., totalling 60.36 g. (77.4% yield).

EXAMPLE VII 9,9-Diethyl-7-bromo-fluorene-2-carboxaldehyde

To a mechanically stirred solution of 9,9-Diethyl-2,7-dibromofluorene (59.38 g., 0.1563 mol.), in THF (325 ml), cooled in dry ice-ethanol bath, n-butyl lithium (104 ml of 1.6 M solution in hexanes, 0.1664 mol, 1.06 eq.) was added dropwise over 25 minutes. After 20 minutes, DMF (17 ml, 0.22 mol.) in THF (30 ml) was added, and the mixture was stirred in the cooling bath for 1.5 hours, and outside the bath for 1 hour. The reaction was then cooled to 5° C., and treated with hydrochloric acid (12.5 ml concentrated HCl diluted with 50 ml water). The mixture was diluted with 200 ml of toluene, and the aqueous phase was separated and extracted with 200 ml of toluene. The combined organic phase was washed with dilute sodium bicarbonate solution, dried over magnesium sulfate and concentrated. The residual solids were recrystallized from heptane-ethyl acetate (9:1), to get colorless solids, 40.29 g. (78.4% yield) m.p. 126–128° C. The mother liquor, after chromatography over 150 g. silicagel, elution with 1:1 heptane-toluene, and trituration of residual solids in hexanes, gave additional product, 6.56 g. (12.8% yield, total 91% yield), m.p. 126–128° C. Mass Spec: mlz 328, 330, (M+). A sample for analysis was prepared by recrystallization from hexanes, m.p. 127–129° C. Analysis calculated for $C_{18}H_{17}BrO$: C, 65.55; H, 5.20; Br, 24.27. Found: C, 65.60; H, 5.51; Br, 24.71.

EXAMPLE VIII 2-(9,9-diethyl-7-bromo-2-) fluorenyl benzothiazole

A mixture of 9,9-diethyl-7-bromo-fluorene-2-carboxaldehyde (49.35 g., 0.15 mol.), 2-amino thiophenol (20 ml. 0.187 mol., 1,25 eq.), and DMSO (110 ml) was heated in an oil bath to a bath temperature of 195° C., held there for 45 minutes, and then poured into water. The separated solids were collected, reslurried in 1:4 acetic acid-water (1000 ml.) filtered, and washed with water and dilute sodium bicarbonate solution. These solids, 80.05 g., were then reslurried in hot ethanol, (600 ml), cooled and filtered to get the product benzothiazole, 45.69 g., m.p. 133.6-135° C. An additional 6.6 g., m.p. 134.6–135.5° C., was obtained by chromatography of the ethanol filtrate. Total recovery 52.29 g. (80.3% yield). Mass Spec: m/z 433, 435, (M+). Analysis calculated for $C_{24}H_{20}BrNS$: C, 66.37; H, 4.64; Br, 18.40; N, 3.23; S, 7.37. Found: C, 66.46; H, 4.52; Br, 18.54; N, 3.14; S, 7.19.

EXAMPLE IX (7-benzothiazol-2-yl-9,9-diethylfluoren-2-vl) diphenylamine

A mixture of 2-(9,9-diethyl-7-bromo-2-) fluorenyl benzothiazole (6.6 g., 0.015 mol.), potassium carbonate (10.3 g.,0.0746 mol.), diphenylamine (4.5 g. 0.0376 mol.), potassium iodide (9.6 g. 0.0173 mol.), copper bronze (2.0 g., 0.0317 mol.), copper (I) iodide (1.5 g., 0.0079 mol.), 18-crown-6 (0.96 g., 0.0036 mol.),and 1,2-dichlorobenzene (45 ml.) was kept at 180–182° C. for 20 hours, cooled and filtered. The filtrate was concentrated and the residue was transferred to a column of silica gel. Elution with heptane gave the product, 3.6 g.(45.5% yield), m.p. 175–178.4° C. Recrystallization from 9:1 heptane-toluene raised the m.p. to 178–180° C. Mass Spec: m/z 522, (M+). Analysis calculated for $C_{36}H_{30}N_2S$: C, 82.76; H, 5.79; N, 5.36; S, 6.12. Found: C, 82.41; H, 5.52; N, 5.25; S, 5.99.

EXAMPLE X (7-benzothiazol-2-yl-9,9-didecylfluoren-2-yl) diphenylamine

The subject compound was prepared generally following the procedures given in Examples VI–VIII, above.

EXAMPLE XI (7-benzothiazol-2-yl-9,9-dioctadecylfluoren-2-yl) diphenylamine

The subject compound was prepared generally following the procedures given in Examples VI–VIII, above.

EXAMPLE XII 9,9-Diethylfluorene

To a mechanically stirred mixture of fluorene (83.2 g. 0.5 mol.), powdered potassium hydroxide (140 g., 2.5 mol.), potassium iodide (4.0 g., 0.024 mol.) and DMSO (225 ml), cooled to 15–20° C., bromoethane (104 ml., 151.84 g., 1.39 mol.) was added over a period of 1.5 hours, and allowed to stir at room temperature overnight. The mixture was diluted with water (1200 ml), and extracted with toluene (2×400 ml). The toluene extract was washed with water, dried and concentrated to get 116.66 g., of a red oil. This was distilled at 1.2 mm, b.p. 125° C. to get a colorless oil, that solidified, 104.32 g., (94 % yield). m.p. 29–30° C. Mass Spec: m/z 222, (M⁺).

EXAMPLE XIII

2-Bromo-9,9-diethylfluorene

To a solution of diethylfluorene (22.2 g., 0.1 mol.) in propylene carbonate (100 ml), N-bromosuccinimide (17.8 g., 0.1 mol.) was added at 57° C. in portions and the mixture was stirred for 30 minutes at 60° C. The mixture was diluted with 1200 ml of water and extracted with 500 ml of toluene. The toluene extract was washed 3 times with 300 ml portions of water, dried and concentrated. The crude product from 3 batches of the same size totaled 117 g. oil. This was distilled at 2 mm. The first fraction, b.p. 90–93° C., 22.33 g., was found to be propylene carbonate. The second fraction, b. p. 155–165° C., 81.0 g. (89.7% yield), was the desired compound. Mass Spec: m/z 300, 302 (M⁺).

EXAMPLE XIV 9,9 Diethyl-2-bromo-7-iodofluorene

A mixture of diethyl monobromofluorene (81.0 g., 0.263 mol.), acetic acid (450 ml), water (47 ml), concentrated sulfuric acid (14 ml), iodine (26.8 g., 0.106 mol.), iodic acid (10.5 g., 0.06 mol.), and carbon tetrachloride (21 ml) was maintained at 80–85° C. for 2.5 hours with mechanical stirring. The product slurry was cooled to room temperature, filtered, and the solids were washed with 1:1 acetic acid-water, and then with water. The air-dried solids weighed 122 g., m.p. 162–164° C. These solids were slurried in 500 ml.of hot methanol for 30 minutes and filtered, 96.94 g. (86.3% yield), m.p. 165.3–166.6° C. Mass Spec: m/z 426,428 (M⁺).

EXAMPLE XV 2-(9,9-Diethyl-7-bromo)-N. N-diphenyl fluoreneamine

A mixture of 9,9 Diethyl-2-bromo-7-iodofluorene (42.7 g., 0.10 mol.), potassium carbonate (60.0g., 0.435 mol.) copper bronze (3.3 g. 0.052 mol), 18-crown-6(2.0 g., 0.0076 mol.), diphenyl amine (20.9 g. 0.1235 mol.) and 1,2-dichlorobenzene (140 ml.) was heated at reflux for 5.5 hours, cooled and filtered. The residue after concentration of the filtrate was transferred to a column of 525 g. silica gel. Elution with hexanes removed the dichlorobenzene, and unreacted bromo iodofluorene, 3.16 g. (7.4%). Elution with toluene-hexane 1:9, gave the product, collected after trituration with methanol, 31.24 g. (67% yield), m.p. 154–156.50 C. Mass Spec: m/z 515 (M⁺iodo diphenylamino fluorene), 467, 469 (M⁺.).

EXAMPLE XVI (7-(4-benzothiazol-2-vlphenyl)-9,9-diethylfluoren-2-yl)diphenylamine A solution of 4-bromophenyl benzothiazole (13.05 g, 0.045 mol.) in THF (150 ml) was cooled to −50° C. To the resulting slurry, n-BuLi (1.6 M in hexane, 33 ml, 0.0528 mol, 1.17 eq.) was added and the mixture stirred for 25 min. The mixture was then allowed to warm to −25°, and then recooled to −78° C. Isopropyl borate (27 ml, 0.117 M) was then added. After 2 hours, the ice cooling bath was removed, and the reaction mixture was allowed to warm to room temperature. The thick light brown slurry which had formed was cooled to 5° C. in an ice-water bath, and a mixture of concentrated hydrochloric acid (15 ml) in 30 ml of water was added. A pale yellow solid separated from the resulting dark brown solution which was filtered and washed with water and ether (50 ml). This crude boronic acid was used without any purification in the next step.

A mixture of diphenylamino-9,9-diethyl-bromofluorene (7.02g, 0.015 mol), benzothiazole boronic acid (7.5 g 0.029 mol.), ethanol (50 ml), in NMP (50 ml) was degassed by bubbling nitrogen through the solution for 20 min. Sodium carbonate (13.0 g, 0.12 mol.) and 5% palladium on charcoal (1.5 g ) were then added, the mixture heated at 85–90° C. for 42 hrs. The resulting solids (18.0 g) that separated upon cooling were collected, washed with ethanol and dried. The solids were then transferred to a chromatograph column containing 300 g of alumina. Elution with 1:1 toluene-heptane gave the product, 4.98 g. (55.5% yield), m.p. 243.6–246.1° C. Recrystallization from toluene did not raise the melting point. Mass Spec: m/z 598, (M⁺). Analysis calculated for $C_{42}H_{34}N_2S$: C, 84.25; H, 5.72; N, 4.68; S, 5.34. Found: C, 83.87; H, 6.02; N, 5.04; S, 5.29.

EXAMPLE XVII (7-(7-benzothiazol-2-yl-9,9-diethylfluoren-2-yl)-9,9-diethylfluoren-2-yl)diphenylamine To a solution of 2-(9,9-diethyl-7-bromo-2-)N,N-diphenyl fluoreneamine (9.4 g., 0.02 mol.), in THF (100 ml), a solution of 1.6M n-butyl lithium in hexanes (14 ml, 0.00224 mol., 1.12 eq.) was added keeping the temperature below −50° C. After 45 minutes a solution of tributyl tin chloride (6 ml, 0.00221 mol.) was added, and the mixture was stirred in the bath for 30 minutes, and outside the bath overnight. After treating with a solution of potassium fluoride at 5° C., the mixture was diluted with 150 ml toluene, the organic phase was washed with water, dried and concentrated to get 15.9 g. of oil. This oil was dissolved in toluene (100 ml) and mixed with 2-(9,9-diethyl-7-bromo-2-) fluorenyl benzothiazole (7.52 g., 0.00173 mol.), degassed, and then treated with bis-triphenyl phosphino palladium (II) chloride (0.68 g., 0.97 mmol.). The mixture was held at 98° C. for 18 hours, cooled, treated with a solution of potassium fluoride, stirred 1 hour, and filtered to remove 5.8 g. of the insoluble tin fluoride. The filtrate was concentrated, and the residue, 22.4 g., was transferred to a column of 350 g. of silica gel. The desired product, 7.6 g. (60% yield) m.p. 217–218.5° C., was obtained on elution with 1:2 toluene-heptane followed by recrystallization from the same solvent mixture. Mass Spec: m/z 742, (M⁺). Analysis: Calculated for $C_{52}H_{46}N_2S$: C 85.45, H 6.34, N 3.83, and S 4.38%. Found, C 85.64, H 6.44, N 3.48, and S 4.01 %.

EXAMPLE XVIII (4-(7-benzothiazol-2-yl-9,9-diethylfluoren-2-yl) phenyl)diphenylamine To a solution of bromotriphenylamine (8.1 g., 0.025 mol.) in THF (125 ml) cooled to below −50° C., a solution of n-butyl lithium in hexanes (18 ml., 0.0288 mol., 1.152 eq.) was added and stirred for 30 minutes. A solution of tributyl tin chloride (8.5 ml, 0.0313, mol.) in THF was added, the mixture was kept in the cooling bath for 1 hour, and then allowed to warm to room temperature. After cooling in an ice bath, a solution of potassium fluoride was added, stirred for 1 hour, diluted with 100 ml of toluene, the organic phase was dried and concentrated to leave 16.3 g. oil. Mass Spec:

m/z 531, 533, 535, (M⁺, organotin). This oil was dissolved in toluene (100 ml), mixed with 2-(9,9-diethyl-7-bromo-2-)fluorenyl benzothiazole, (9.0 g., 0.0207 mol.) and bistriphenyl phosphino palladium (II) chloride (0.9 g., 0.0013 mol.) and held at 95–100C. for 18 hours. After cooling, the mixture was treated with a solution of potassium fluoride, stirred one hour, and the insoluble fluoride (9.19 g.) was filtered off. The filtrate was concentrated, and the residue was transferred to a column of silica gel. Elution with heptane removed 1.43 g. (18%) yield), m.p. 95–97° C. of a material identified as diphenylamino biphenyl; Mass Spec: m/z 321 (M⁺). Elution with toluene:heptane 1:4 gave 0.35 g., m.p. 185–195° C., identified as tetraphenyl benzidine; Mass Spec: m/z 488 (M⁺). The desired product was obtained on elution with toluene:heptane 1:1, followed by recrystallization from the same solvent, 7.66 g. (64% yield), m.p.205.5–208° C. Mass Spec: m/z 598, (M⁺), 569 (M—$C_2H_5$), 554 (M—$CH_3$). Analysis: Calculated for $C_{42}H_{34}N_2S$, C 84.25, H 5.72, N 4.68, and S 5.34%. Found, C 84.52, H 5.54, N 4.48, and S 5.35 %.

EXAMPLE XIX 7-(2-Benzothiazolyl)-9,9-diethylfluorene-2-boronic acid

To a solution of 2-(9,9-diethyl-7-bromo-2-)fluorenyl benzothiazole, (19.5 g., 0.045. mol.), in THF (240 ml), cooled in a dry ice-acetone bath, a solution of n-butyl lithium in hexanes (33 ml, 0.0528 mol., 1.173 eq.) was added dropwise, and after 25 minutes, tri-isopropyl borate (27 ml., 0.117 mol.) was syringed in. After 3 hours, the cooling bath was removed, and on warming to 5° C., the brown slurry turned into a green solution, and at 20° C. (in 1 hour), a brown solution resulted. This was cooled to 5° C. and treated with a mixture of 15 ml, concentrated hydrochloric acid and 25 ml water. The THF layer was separated, and the aqueous layer was extracted with 200 ml ether. The combined organic phase was concentrated, the residual solids were suspended in toluene, filtered, and washed with toluene, 17.0 g., m.p. 160–163° C. ( quantitative yield).

EXAMPLE XX 7-(2-Benzothiazolyl)-9,9-diethyl-2-fluorenyl tributyl tin

To a magnetically stirred solution of 2-(9,9-diethyl-7-bromo-2-)fluorenyl benzothiazole, (6.5 g., 0.015 mol.) in THF (70 ml.), cooled to −65° C., a solution of n-butyl lithium in hexanes (10 ml, 0.016 mol.) was added. After 30 minutes a solution of tributyl tin chloride (4.4 ml, 0.0162 mol.) in THF (10 ml.) was added, and the mixture was allowed to warm to room temperature overnight. The mixture was cooled in an ice-water bath, treated with a solution of potassium fluoride, stirred one hour, diluted with 1:1 toluene-heptane, the organic phase was dried, and concentrated to leave an oil. This oil was transferred to a column of 200 g., alumina, and the column eluted with heptane to get the desired organo tin product as a viscous colorless oil, 7.6 g. (78% yield). Mass Spec: m/z 641, 643, 645, (M⁺).

EXAMPLE XXI 7-(2-Benzothiazolyl)-9,9-didecyl-2'-bromo-2,7+-bifluorenyl (Using an organotin compound) The organo tin fluorenyl compound from the above procedure, 25.3 g., was prepared from 2-(9,9-diethyl-7-bromo-2-)fluorenyl benzothiazole, (13.0 g., 0.030 mol.). This compound was used without purification and was dissolved in toluene (100 ml.), degassed and treated with 9,9-didecyl-2,7-dibromofluorene (20.0 g. 0.0331 mol.), bistriphenylphosphino palladium (II) chloride (0.76 g., 0.0011 mol.), and triphenyl phosphine (0.26 g., 0.0010 mol.). The resulting mixture was held at 90° C. for 18 hours, and the temperature raised to reflux and maintained there for 5 hours. After cooling, treatment with potassium fluoride, filtration and concentration of the filtrate, the residue was chromatographed over 600 g. of silica gel. Elution of the column with heptane removed the starting dibromo compound, and with 1:3 toluene-heptane, gave impure product, 5.79 g., m.p. 121–123.6° C. A second column chromatography using 1:1 toluene-heptane as the eluent gave the desired product as a third fraction which after 2 recrystallizations from heptane had a m.p.121.6–123.4° C. Mass Spec: m/z 877, 879, (M⁺). Analysis: Calculated for $C_{57}H_{68}NBrS$: C, 77.87; H, 7.80; N, 1.59; Br, 9.09; S, 3.65. Found: C, 78.17; H, 7.83; N, 1.35; Br, 9.27; S, 3.61.

EXAMPLE XXII 7-(2-Benzothiazolyl)-9,9-didecyl-2+-bromo-2,7'-bifluorenyl (Usinq a boronic acid intermediate) A mixture of dibromo didecyl fluorene, (3.0 g.), 7-(2-benzothiazolyl)-9,9-diethylfluorene-2-boronic acid, (2.0 g.), bis triphenyl phosphino palladium (II) chloride (0.175 g.), triphenyl phosphine (0.13 g.) dimethoxyethane, (25 ml.) and a solution of sodium carbonate (1.0 g.) in water (5 ml), was kept at reflux overnight, diluted with toluene, filtered, and the filtrate was concentrated. The residue was chromatographed on silica gel. After elution with heptane to remove the unreacted dibromofluorene, further elution with heptane toluene (1:3), gave a second fraction containing the desired product, 1.42 g., m.p. 124.3–126.5° C. Mass Spec: m/z 877, 879, (M⁺)

EXAMPLE XXIII (7-(7-(7-benzoth iazol-2-yl-9,9-diethylfluoren-2-yl)-9,9-didecylfluoren-2-yl)9,9- diethylfluoren-2-yl) diphenylamine To a solution of 2-(9,9-diethyl-7-bromo-2-)N,N-diphenyl fluoreneamine (4.7 g.,0.010 mol.), in THF (50 ml.), cooled in a dry ice-ethanol bath, a solution of n-butyl lithium in hexanes (1.6 M, 7 ml, 0.0112 mol.)was added. After 25 minutes, a solution of tributyl tin chloride (3.5 ml, 0.0130 mol.) in THF (5 ml.) was added, and after 2 hours, the cooling bath was removed. When the mixture was at 5° C., a solution of potassium fluoride was added, stirred for 1 hour, and then the organic phase was dried and concentrated to get the organotin as an oil, 8.27 g. This oil was dissolved in toluene (60 ml.), mixed with bromobifluorenyl benzothiazole (6.6 g.,0.0075 mol.) and bis(triphenylphosphine) palladium (II) chloride (0.3 g., 0.43 mmol.) and the mixture was held at 90° C. overnight. Addition of potassium fluoride caused the precipitation of 3.33 g. of insoluble floride. The toluene filtrate was concentrated and the residue was chromatographed on 200 g. of silica gel. Elution with heptane and 4:1 heptane-toluene removed most of the by-products. The product was eluted out with 3:1 and 1:1 toluene-heptane and recrystallized from 1;1 toluene heptane, 4.25 g., (47.6% yield), m.p. 226.4–228.8° C. A second recrystallization raised the m.p. to 229.2–230.9° C. Analysis: Calculated for $C_{86}H_{94}N_2S$: C, 86.97; H, 7.98; N, 2.36; S, 2.69. Found: C, 87.16; H, 7.95; N, 2.51; S, 2.63.

EXAMPLE XXIV (7-(7-(7-benzothiazol-2-yl-9,9-diethylfluoren-2-yl)-9,9-didecylfluoren-2-yl)9,9-diethylfluoren-2-yl) diphenylamine (Alternate Synthesis)

To a solution of 7-diphenylamino-9,9-diethyl-2-bromofluorene, (9.4 g., 0.020 mol.), in THF (100 ml.), a 1.6 M solution of n-butyl lithium in hexanes (14 ml., 0.0224 mol.) was added with dry ice-ethanol cooling, and after 45 minutes, a solution of tributyl tin chloride (6 ml, 0.0221 mol.) in THF (10 ml), was added. After 30 minutes, the cooling bath was removed, and the mixture was stirred for 2 hours. The mixture was then cooled to 5° C., treated with potassium fluoride, and diluted with toluene. The organic phase was dried and concentrated to leave an oil, 15.9 g. This oil was dissolved in toluene (120 ml), degassed, mixed with dibromo didecylfluorene (24.16 g.) and tetrakis triphenylphosphino palladium(0), (0.49 g.) and the mixture held at 100° C. for 18 hours. After cooling, a solution of potassium fluoride was added, and the insoluble tin fluoride (6.0 g.) was removed by filtration. The filtrate was concentrated, and the residue was transferred to a column of 900 g. of alumina. Elution with 1000 ml of heptane returned 14.9 g. of the unreacted dibromofluorene. Elution with 9:1 heptane-toluene gave the product 13.64 g. (74.8% yield) as a thick oil. Mass Spec: m/z 911, 913, ($M^+$). This material was used in the next example without further purification.

A mixture of 7'-diphenylamino-9,9-diethyl-9 ', 9'-didecyl-2-bromo-2', 7-bifluorenyl, (5.14 g.), benzothiazolyl fluorenyl boronic acid (3.7 g.), NMP (15 ml), 10% Pd/C (reduced 0.4 g.) and sodium carbonate (3.2 g.), was held at 900C for 24 hours, cooled, diluted with toluene and filtered. The toluene filtrate was washed with water, dried over magnesium sulfate and concentrated. The residue was chromatographed on 200 g. of silica gel. Elution with 2:1 heptane-toluene, gave the product, which was then recrystallized from 1:1 heptane toluene to give 1.6g. (27% yield) of the product, m.p. 227.5–229.2° C.

EXAMPLE XXV 9,9-Diethyl-N, N-diphenyl-7-(2-benzoazolyl)-2-fluoreneamine

A mixture of cesium carbonate (6.5 g. 20 mmol, dried at 190° C. under 1 mm), 9,9-diethyl-N,N-diphenyl-7-bromo-2-fluoreneamine (7.4 g., 16 mmol), benzoxazole (2.4 g., 20 mmol), copper(l) iodide (0.38 g., 2 mmol), palladium (II) acetate (0.075 g., 0.334 mmol), triphenyl phosphine (0.15 g., 0.6 mmol) and DMF (30 ml) was kept at 115° C. for 18 hours under an atmosphere of nitrogen, then cooled, diluted with toluene and filtered. The filtrate was washed with water, dried and concentrated. The residue was chromatographed on alumina. Earlier fractions gave 0.25 g., m.p. 102–104° C., identified as 2-phenyl benzoxazole (m/z 195). Elution with heptane-toluene (3:1), followed by crystallization, gave 5.14 g. (65% yield) of bright yellow crystals, m.p. 193–194° C. A sample for analysis was obtained by sublimation under 0.5 mm vacuum at a bath temperature of 210° C. Mass Spec: mlz 506 ($M^+$). Analysis: Calculated for $C_{36}H_{30}N_2O$: C, 85.34; H, 5.97; N, 5.53. Found: C, 85.25; H, 5.97; N, 5.55.

EXAMPLE XXVI

Determination of 2-Photon Absorption Cross-Section

The two photon absorption coefficients $\beta$ and the molecular two-photon cross-section $\sigma_2$ were determined from an experimental measurement of the transmitted intensity of a laser beam at 800 nm as a function of the incident intensity. The data are presented in Table I, below. According to the basic theoretical consideration, the two-photon absorption (TPA) induced decrease in transmissivity can be expressed as $$I(L) = I_o(1 + I_o L \beta) \tag{1}$$

where $I(L)$ is the transmitted beam intensity, $I_o$ the incident beam intensity, L the thickness of the sample, and $\beta$ is the TPA coefficient of the sample medium. In the derivation of the above equation it is assumed that the linear attenuation of the medium can be neglected and the beam has a nearly uniform transverse intensity distribution within the medium. The TPA coefficient can be determined by measuring the transmitted intensity $I(L)$ as a function of various incident intensities $I_o$ for a given medium with a given L value. The TPA coefficient $\beta$ (in units of cm/GW) of a given sample is determined by $$\beta = \sigma_2 N_o = \sigma_2 N_A d_0 \times 10^{-3} \tag{2}$$

where $N_o$ is the molecular density of the material being measured (in units of $1/cm^3$), $\sigma_2$, is the molecular TPA cross-section of the same material (in units of $cm^4/GW$), $d_0$ is the concentration of the material (in units of M/L) and finally $N_A$, Avogadro's number. For known $\beta$ and $d_0$, the value of $\sigma_2$ can be easily calculated from equation (2).

In practice, various optical detectors such as photodiodes, photomultipliers, photometers and optical power meters can be used to measure the incident beam intensity $I_o$ and the transmitted beam intensity $I(L)$ separately. The change of the $I_o$ values can be done by using variable optical attenuators (such as neutral filters or rotatable polarizing prisms), or by varying the beam cross-section of the input laser beam (by changing the relative distance of the sample to the focal point of the input beam). The input laser beam used for the experimental measurements was a pulsed laser dye system with a wavelength of 800 nm, a spectral width of 1–10 nm, a pulse duration of 8 ns, a beam size (before focusing lens) of 3–5 nm, a beam divergency of 1.2–1.5 mrad, and a repetition rate between 1–30 Hz.

TABLE I

| | Nonlinear Optical Properties (wavelength 800 nm, solvent (THF)) | | | |
|---|---|---|---|---|
| Chromophore (Example) | $\lambda_{max}$ (nm) Linear Abs. (Upconv. Emission) | $\beta$ cm/GW at 0.2 mol/L | $\sigma_2'(\times 10^{-48}$ $cm^4 \cdot sec$ ph $\cdot$ molecule) | $\sigma_2'/MW(\times 10^{-50}$ $cm^4 \cdot sec \cdot mole$ ph $\cdot$ molecule $\cdot$ g) |
| IV | 395 (475) | 4.6 | 95.5 | 21 |
| V | 406.5 (517) | 2.3 | 47.1 | 11 |

TABLE I-continued

Nonlinear Optical Properties (wavelength 800 nm, solvent (THF))

| Chromophore (Example) | $\lambda_{max}$ (nm) Linear Abs. (Upconv. Emission) | $\beta$ cm/GW at 0.2 mol/L | $\sigma_2'(\times 10^{-48}$ cm$^4$·sec ph · molecule) | $\sigma_2'/MW(\times 10^{-50}$ cm$^4$·sec·mole ph · molecule · g) |
|---|---|---|---|---|
| IX | 391.5 (479) | 4.7 | 97.5 | 19 |
| X | 391 (481) | 5.4 | 110.6 | 15 |
| XI | 391 (490) | 4.2 | 87.0 | 8.9 |
| XVIII | 376.5 (485) | 5.1 | 105.2 | 17.5 |
| XVI | 379 (498) | 4.8 | 99.2 | 16.6 |
| XVII | 384 (491) | 6.2 | 127.9 | 17.5 |
| XXIII | 384 (465) | 4.0 | 81.8 | 6.9 |

In the above table, the term $\sigma_2'$ represents $h\nu\sigma_2$, i.e., the value $\sigma_2$ multiplied by the energy of the incident photon at 800 nm to remove the energy terms from the units.

These data clearly show increased size of the 2-photon cross-section as compared to most state-of-the-art organic compounds. The increased cross-section, when coupled with strong upconverted fluorescence, makes these chromophores more useful in fluorescent imaging application such as 2-photon laser scanning confocal microscopy where strong fluorescence is needed to obtain high resolution. Large 2-photon absorption cross-sections also lead to greatly improved optical limiting behavior. In addition the long chain alkyl groups incorporated into these materials lead to very high solubility in organic solvents and good compatibility with organic polymers. Solubility of these chromophores is generally at least 0.01 and up to about 35% in common organic solvents.

Two-photon absorbing dyes which exhibit upconverted fluorescence have also found use in other areas of photonic technology. These include 2-photon pumped upconverted lasing, 2-photon confocal microscopy, 2-photon photodynamic therapy, 2-photon optical power limiting, and 3D optical data storage.

Various modifications may be made in the instant invention without departing from the spirit and scope of the appended claims.

What is claimed is:

1. A two-photon absorbing chromophore of the formula

D—Ar—A wherein Ar is selected from the group consisting of

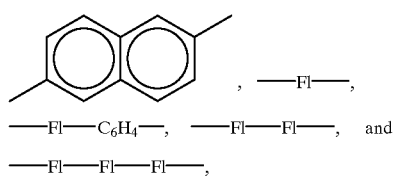

wherein Fl is a fluorene group of the formula:

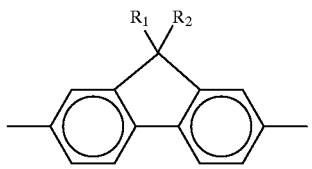

wherein $R_1$ and $R_2$ are alkyl groups having 2 to 20 carbon atoms, and wherein $R_1$ and $R_2$ are the same or different;

wherein D is

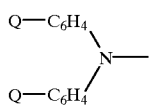

wherein Q is selected from the group consisting of —H, —OH and —O—C$_x$H$_{2x+1}$, wherein x has a value of 1 to 10; and wherein A is selected from the group consisting of

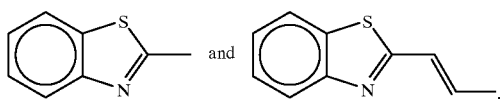

2. The chromophore of claim 1 wherein Ar is

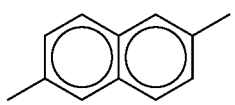

and A is

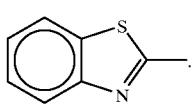

3. The chromophore of claim 1 wherein Ar is

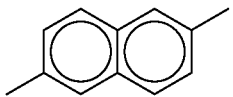

and A is

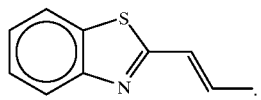

4. The chromophore of claim 1 wherein Ar is —Fl—, wherein $R_1$ and $R_2$ are —$C_2H_5$, and wherein A is

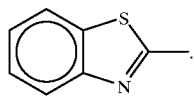

5. The chromophore of claim 1 wherein Ar is —Fl—, wherein $R_1$ and $R_2$ are —$C_{10}H_{21}$, and wherein A is

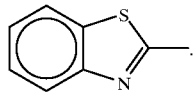

6. The chromophore of claim 1 wherein Ar is —Fl—, wherein $R_1$ and $R_2$ are —$C_{18}H_{37}$, and wherein A is

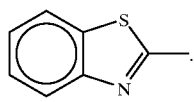

7. The chromophore of claim 1 wherein Ar is —Fl—$C_6H_4$—, wherein $R_1$ and $R_2$ are —$C_2H_5$, and wherein A is

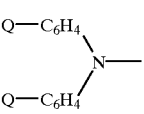

8. The chromophore of claim 1 wherein Ar is —Fl—Fl—, wherein $R_1$ and $R_2$ are —$C_2H_5$, and wherein A is

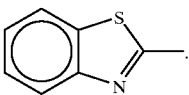

9. The chromophore of claim 1 wherein Ar is

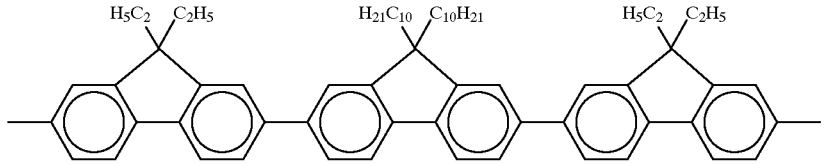

and wherein A is

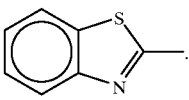

10. A two-photon absorbing chromophore of the formula

D—Ar—A wherein Ar is selected from the group consisting of

 Fl—, —Fl—$C_6H_4$—, —Fl—Fl—, and —Fl—Fl—Fl—, wherein Fl is a fluorene group of the formula:

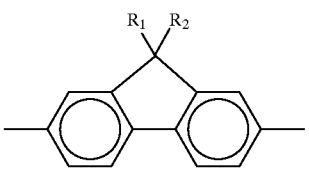

wherein $R_1$ and $R_2$ are alkyl groups having 2 to 20 carbon atoms, and wherein $R_1$ and $R_2$ are the same or different; wherein D is

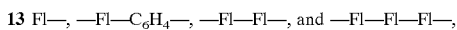

wherein Q is selected from the group consisting of —H, —OH and —O—$C_xH_{2x+1}$, wherein x has a value of 1 to 10; and wherein A is selected from the group consisting of

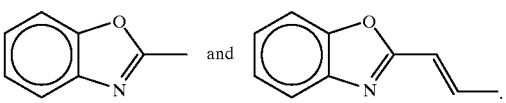

* * * * *